United States Patent
Hsu

(10) Patent No.: US 11,000,483 B2
(45) Date of Patent: May 11, 2021

(54) TRANSDERMAL PATCH

(71) Applicant: TEH SENG PHARMACEUTICAL MFG, CO., LTD., Tainan (TW)

(72) Inventor: Shih-Pin Hsu, Tainan (TW)

(73) Assignee: TEH SENG PHARMACEUTICAL MFG, CO., LTD., Tainan (TW)

( * ) Notice: Subject to any disclaimer, the term of this patent is extended or adjusted under 35 U.S.C. 154(b) by 0 days.

(21) Appl. No.: 16/590,620

(22) Filed: Oct. 2, 2019

(65) Prior Publication Data
US 2020/0155476 A1 May 21, 2020

(30) Foreign Application Priority Data

Nov. 16, 2018 (TW) .................................. 107140732

(51) Int. Cl.
*A61K 31/27* (2006.01)
*A61K 9/70* (2006.01)
*A61K 47/14* (2017.01)
*A61K 47/10* (2017.01)

(52) U.S. Cl.
CPC ............ *A61K 9/7061* (2013.01); *A61K 31/27* (2013.01); *A61K 47/10* (2013.01); *A61K 47/14* (2013.01)

(58) Field of Classification Search
CPC .................................................... A61K 31/27
See application file for complete search history.

(56) References Cited

U.S. PATENT DOCUMENTS

2010/0087768 A1* 4/2010 Forlano ................. A61P 25/16
602/48
2011/0313372 A1* 12/2011 Eifler .................... A61K 31/13
604/304

FOREIGN PATENT DOCUMENTS

CN 104136025 A 11/2014
TW 201505665 A 2/2015

* cited by examiner

*Primary Examiner* — Benjamin J Packard
(74) *Attorney, Agent, or Firm* — Bacon & Thomas, PLLC

(57) ABSTRACT

The present invention provides a transdermal patch including: a backing layer; a drug-containing adhesive layer including rivastigmine or a pharmaceutically acceptable salt thereof and two kinds of skin penetration enhancers; and a release liner; wherein the drug-containing adhesive layer is disposed between the backing layer and the release liner; a content of rivastigmine or the pharmaceutically acceptable salt thereof is between 10 wt % and 30 wt % based on a total weight of the drug-containing adhesive layer; and the adhesive includes a pressure sensitive adhesive.

9 Claims, 1 Drawing Sheet

TRANSDERMAL PATCH

CROSS REFERENCE TO RELATED APPLICATION

This application claims the benefits of the Taiwan Patent Application Serial Number 107140732, filed on Nov. 16, 2018, the subject matter of which is incorporated herein by reference.

BACKGROUND OF THE INVENTION

1. Field of the Invention

The present invention relates to a transdermal patch and, more particularly, to a transdermal patch comprising rivastigmine.

2. Description of Related Art

Alzheimer's disease (AD) is the most common dementia caused by neurodegenerative diseases in the elderly. Because of progressive cognitive decline and memory loss, it takes a high social cost in the treatment of the disease and in the care of patients' daily lives.

Regarding the pharmacotherapy nowadays, there are available medicines for preserving or improving cognition though Alzheimer's disease cannot be completely cured. At present, the medicines approved by USFDA are categorized into two types, one of which is cholinesterase inhibitors including rivastigmine, donepezil, and galantamine, and another one of which is acceptor antagonists of N-methyl-D-aspartate (NMDA) including memantine.

Rivastigmine, i.e. (S)-3-[1-(dimethylamino)ethyl]phenyl N-ethyl-N-methylcarbamate, inhibits both acetylcholinesterase and butyrylcholinesterase at the same time. By inhibiting cholinesterase-mediated decomposition of acetylcholine, rivastigmine improves the durability of acetylcholine in the brain and is therefore used as a medicine to preserve or improve cognition.

Although there exist commercially available patches (for example, Exelon®) for Alzheimer's disease, the preparation of such patches is complicated because that the patch is consisted of a backing layer, a drug-containing layer, an adhesive layer and a release liner, and the drug-containing layer and the adhesive layer are separate and formed by conducting the coating process twice. In contrast, the drug-containing adhesive layer of the patch according to the present invention comprises an adhesive and a drug, so that it is not necessary to prepare the drug-containing layer and adhesive layer separately. Therefore, its preparation is simple and saves time and cost and is favorable for mass production. In addition, the present invention also provides another option for consumers.

SUMMARY OF THE INVENTION

One object of the present invention is to provide a transdermal patch which does not have the disadvantage of occurring tolerance caused by long-term administration of oral medication, and can assist in the treatment or effectively delay the deterioration of the disease, such as Alzheimer's disease or other neurodegenerative diseases.

One object of the present invention is to provide a transdermal patch, comprising: a backing layer; a drug-containing adhesive layer, comprising: rivastigmine or a pharmaceutically acceptable salt thereof, an adhesive, and two kinds of skin penetration enhancers; and a release liner, wherein the drug-containing adhesive layer is disposed between the backing layer and the release liner, a content of rivastigmine or the pharmaceutically acceptable salt thereof is in a range from 10 wt % to 30 wt % based on a total weight of the drug-containing adhesive layer, and the adhesive comprises a pressure sensitive adhesive.

In the transdermal patch according to one aspect of the present invention, the content of rivastigmine or the pharmaceutically acceptable salt thereof may be in a range from 10 wt % to 30 wt %, preferably 15 wt % to 25 wt %, and more preferably 18 wt % to 22 wt %, based on the total weight of the drug-containing adhesive layer.

In the transdermal patch according to one aspect of the present invention, a content of the adhesive may be in a range from 50 wt % to 80 wt %, and preferably 60 wt % to 76 wt %, based on the total weight of the drug-containing adhesive layer.

In the transdermal patch according to one aspect of the present invention, the pressure sensitive adhesive is not limited and may, by way of example and not limitation, be a rubber-based pressure sensitive adhesive, an acrylic-based pressure sensitive adhesive, a polyurethane-based pressure sensitive adhesive, a silicon-based pressure sensitive adhesive, a hydrogel containing an aqueous polymer or a combination thereof. Preferably, the pressure sensitive adhesive is an acrylic-based pressure sensitive adhesive.

In the transdermal patch according to one aspect of the present invention, preferably, the pressure-sensitive adhesive is an acrylic-based pressure sensitive adhesive.

In the transdermal patch according to one aspect of the present invention, the two kinds of skin penetration enhancers may be selected from the group consisting of diethylene glycol monoethyl ether, glyceryl monooleate, glycerin, glyceride, fatty acid, fatty acid salt, azone, diethyltoluamide, propanediol, propylene glycol ester, butanediol, isopropyl ester, and urea. Preferably, the two kinds of skin penetration enhancers are diethylene glycol monoethyl ether and glyceryl monooleate.

In the transdermal patch according to one aspect of the present invention, a content of the two kinds of skin penetration enhancers may be in a range from 0.1 wt % to 10 wt %, and preferably 1 wt % to 5 wt %, based on the total weight of the drug-containing adhesive layer.

In the transdermal patch according to one aspect of the present invention, the drug-containing adhesive layer may further comprise a tacking agent. Preferably, the tacking agent is a resin.

Furthermore, a content of the tacking agent may be in a range from 0.1 wt % to 10 wt %, and preferably 2 wt % to 10 wt %, based on the total weight of the drug-containing adhesive layer. If the content of the tacking agent is greater than 10 wt %, it may slow the release of rivastigmine. Moreover, the drug-containing adhesive layer cannot be formed if the content of the tacking agent is less than 0.1 wt %.

Another object of the present invention is to provide a transdermal patch, comprising: a backing layer; a drug-containing adhesive layer, comprising 10-30 wt % of rivastigmine or a pharmaceutically acceptable salt thereof; 50-80 wt % of an acrylic-based pressure sensitive adhesive; 0.1-10 wt % of two skin penetration enhancers; and 0.1-10 wt % of a tacking agent; and a release layer, wherein the drug-containing adhesive layer is disposed between the backing layer and the release liner.

In the transdermal patch according to one aspect of the present invention, the backing layer may be a film, a sheet, a sheet-like porous product, a sheet-like foaming product, a fabric, a woven fabric, or a nonwoven fabric made of a synthetic resin selected from the group consisting of polyethylene, polypropylene, polybutadiene, ethylene-vinyl acetate copolymers, vinyl acetate-vinyl chloride copolymers, polyvinyl chloride, polyimide, polyester, nylon, cellulose derivatives, and polyurethane, as well as a laminate of the foregoing or paper.

In the transdermal patch according to one aspect of the present invention, the release liner preferably is a silicon-coated PET liner. However, the present invention is not limited thereto.

According to one aspect of the present invention, the acrylic-based pressure sensitive adhesive may be selected from the group consisting of Duro-Tak® 87-2353, Duro-Tak® 387-2353, Duro-Tak® 87-900A, Duro-Tak® 87-9301, Duro-Tak® 87-4098, Duro-Tak® 87-2510, Duro-Tak® 387-2510, Duro-TA® 87-2287, Duro-Tak® 387-2287, Duro-Tak® 87-4287, Duro-Tak® 87-2516, Duro-Tak® 387-2516, Duro-Tak® 87-2074, Duro-Tak® 87-235A, Duro-Tak® 87-2852, Duro-Tak® 87-2051, Duro-Tak® 387-2051, Duro-Tak® 87-2052, Duro-Tak® 387-2052, Duro-Tak® 87-2054, Duro-Tak® 387-2054, Duro-Tak® 87-2194, Duro-Tak® 87-2196, and a combination thereof.

In the transdermal patch according to one aspect of the present invention, the overall composition may further comprise one or more selected from the group consisting of a stabilizer, a dye, a pigment, aninert filler, a gel former and an antioxidant.

Yet another object of the present invention is to provide a use of rivastigmine for preparing the transdermal patch described above.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
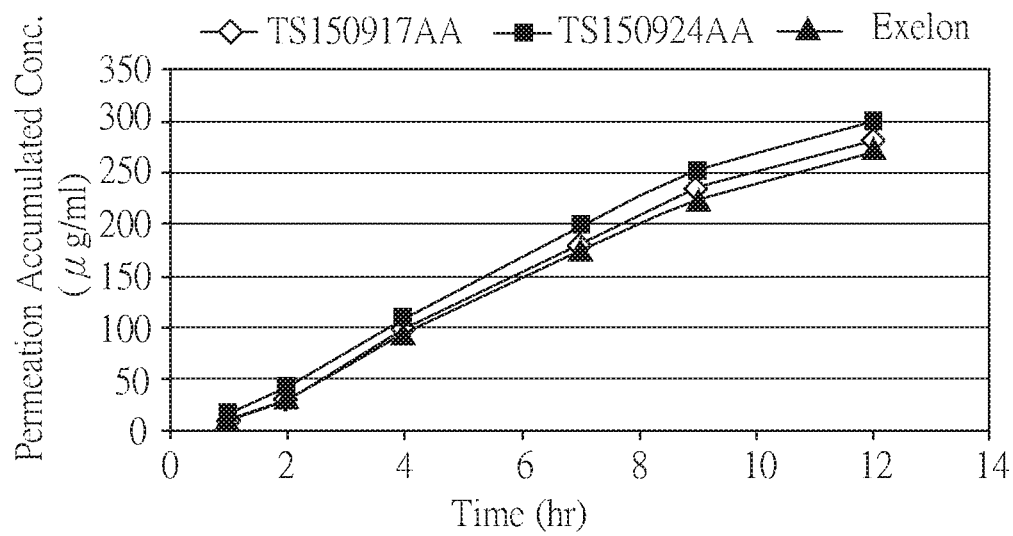
FIG. 1 is a graph showing the accumulated concentration of rivastigmine in the in vitro skin permeation testing for patches (TS150917AA and TS150924AA) of an embodiment of the present invention and for a commercial patch Exelon® at different time points.

The invention will be more specifically described by embodiments, but such embodiments are not intended to limit the scope of the present invention. Unless otherwise specified, the "%" indicating the content of the components and the mass of the subjects in the following examples and comparative examples is based on the weight.

The chemical formula of rivastigmine is $C_{14}H_{22}N_2O_2$, and can be represented by the following structural formula:

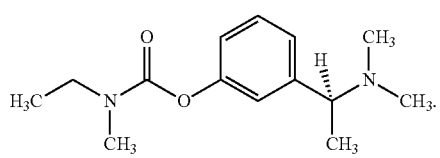 [SMILES: CCN(C)C(=O)Oc1cccc([C@H](C)N(C)C)c1]

Preparation of a Transdermal Patch

First, the rivastigmine base was mixed with an organic solvent, wherein the organic solvent was 2-4 times the amount of the rivastigmine base. A skin penetration enhancer was then added, followed by the addition of a resin, and then thoroughly stirred until the complete dissolution. Then, an acrylic-based pressure sensitive adhesive was added, and a mixture was obtained after stir and mix.

The organic solvent may, by way of example and not limitation, comprise chloroform, dichloromethane or ethyl acetate. Preferably, the skin penetration enhancer is diethylene glycol monoethyl ether and glyceryl monooleate; and, the tacking agent preferably is a resin. The acrylic-based pressure sensitive adhesive may comprise: Duro-Tak® 87-2353, Duro-Tak® 387-2353, Duro-Tak® 87-900A, Duro-Tak® 87-9301, Duro-Tak® 87-4098, Duro-Tak® 87-2510, Duro-Tak® 387-2510, Duro-Tak® 87-2287, Duro-Tak® 387-2287, Duro-Tak® 87-4287, Duro-Tak® 87-2516, Duro-Tak® 387-2516, Duro-Tak® 87-2074, Duro-Tak® 87-235A, Duro-Tak® 87-2852, Duro-Tak® 87-2051, Duro-Tak® 387-2051, Duro-Tak® 87-2052, Duro-Tak® 387-2052, Duro-Tak® 87-2054, Dura-Tak® 387-2054, Duro-Tak® 87-2194, or Dura-Tak® 87-2196. However, the present invention is not limited thereto.

To prepare a transdermal patch, said mixture was applied to a suitable backing layer and dried at a temperature of 90 to 100° C. for 20 minutes to remove the organic solvent. The dried coating had a weight of about 0.004 mg/cm². Finally, a release liner was applied and the transdermal patch was punched out to the desired size.

PREPARATION EXAMPLE

To prepare the drug-containing adhesive layer of a transdermal patch, a rivastigmine base was mixed with the ethyl acetate, wherein the ethyl acetate was 3 times the amount of the rivastigmine base. Diethylene glycol monoethyl ether and glyceryl monooleate were then added, followed by the addition of a resin, and then thoroughly stirred until the complete dissolution. Afterward, Duro-Tak 387-2516 was added, and a formulation was obtained after stir and mix. In addition, the component ratio of the drug-containing adhesive layer is 20 wt % of rivastigmine base, 2 wt % of diethylene glycol monoethyl ether, 1 wt % of glycerol monooleate, 72 wt % of Duro-Tak 387-2516, and 5 wt % of resin, as shown in Table 1 below.

TABLE 1

| Composition | wt % |
|---|---|
| Rivastigmine base | 20 |
| Diethylene glycol monoethyl ether | 2 |
| Glyceryl monooleate | 1 |
| Duro-Tak 387-2516 | 72 |
| Resin | 5 |

To prepare a transdermal patch, said formulation was applied to a suitable backing layer and dried at a temperature of 90 to 100° C. for 20 minutes to remove the organic solvent. The dried coating had a weight of about 0.004 mg/cm² and a coating thickness of 215 μm. Finally, a release liner was applied and the transdermal patch was punched out to obtain the transdermal patch. Furthermore, batch numbers TS150917AA, TS150917AA2, and TS150924AA represented patches manufactured according to the aforementioned preparation process, the three had the same composition ratio, and only the batch numbers were different.

TEST EXAMPLE 1

In Vitro Skin Permeation Testing

To determine the skin permeability of rivastigmine of the transdermal patch according to the present invention, an in vitro skin permeation testing was conducted. The abdominal skin of SD rat (Medgaea Life Sciences Ltd.) was mounted to a Franz diffusion cell, and a transdermal patch was attached to the abdominal skin of SD rat after removing the release liner. Phosphate buffer (pH 4.5) was injected to the Franz diffusion cell as a receptor solution, and the testing temperature was 32° C. At each sampling time point (1 hour, 2 hours, 4 hours, 7 hours, 9 hours, and 12 hours), 10 ml of the receptor solution was taken from the Franz diffusion cell and replaced with a new 10 ml receptor solution. The content of rivastigmine in the sample was analyzed by high-performance liquid chromatography (HPLC) using a C18 column (column size: 250 mm×4.6 mm, particle size: 5 μm), 20 μl of the sample was injected into the column, and the signal was detected at a wavelength of 225 nm. The mobile phase was consisted of 0.1% (v/v) phosphoric acid solution and methanol in a ratio of 1:1.

FIG. 1 is a graph showing the accumulated concentration of rivastigmine in the in vitro skin permeation testing for the patches (TS150917AA and TS150924AA) of the embodiment of the present invention and for a commercial patch Exelon® at different time points. As shown in FIG. 1, the transdermal patches of the present invention had a similar or even better skin permeability of rivastigmine compared to the control group of Exelon®.

TEST EXAMPLE 2

Dissolution Testing

The release liner of the transdermal patch obtained from the Preparation Example was removed, and then the patch was placed in a dissolution machine for a dissolution testing. Potassium dihydrogen phosphate (20 mM, pH 4.5) was used in the dissolution machine as a solution, and the testing was conducted at a rotation speed of 50 rpm with the testing temperature of 32° C. The samples were taken at different time points (1 hour, 2 hours, 4 hours, 7 hours, 9 hours, and 12 hours) from the start of the testing, and then the dissolution of the patch was determined by HPLC.

Figure 2:
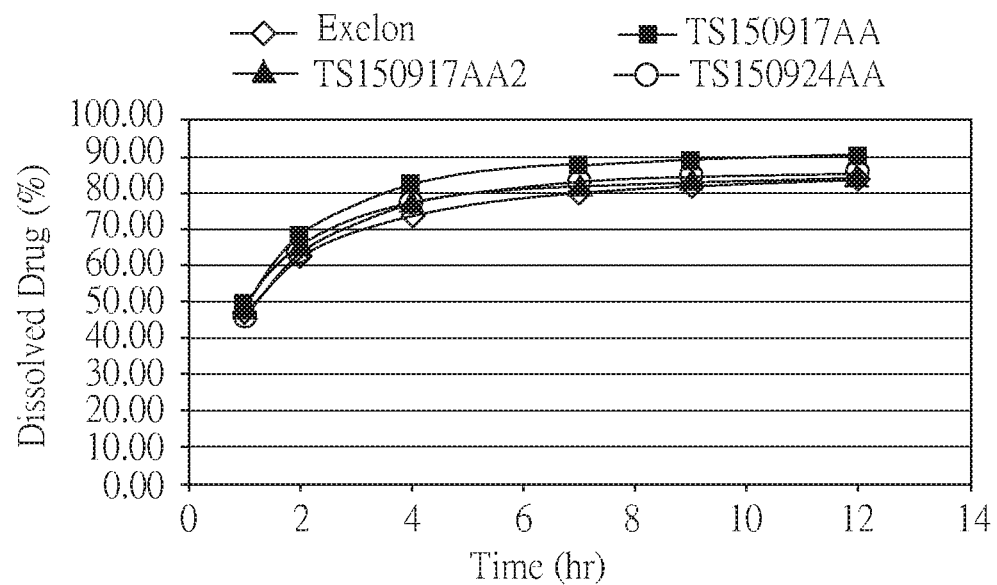
FIG. 2 is a graph showing the dissolution, measured in the different time points, for patches (TS150917AA, TS150917AA2 and TS150924AA) of an embodiment of the present invention and for a commercial patch Exelon®.

FIG. 2 is a graph showing the dissolution, measured in the different time points, for the patches (TS150917AA, TS150917AA2 and TS150924AA) of the embodiment of the present invention and for a commercial patch Exelon® in a dissolution testing. As shown in FIG. 2, the transdermal patch of the present invention has a similar or better rivastigmine dissolution than that of the control group of Exelon®.

TEST EXAMPLE 3

Bioequivalence Trial

To determine whether the transdermal patch of the present invention has similar bioavailability to that of commercial Exelon®, a bioequivalence trial was conducted. This trial was a randomized two way crossover design. First, 28 healthy adults were randomly divided into two sequences. One of the sequences was to administer Exelon® (4.6 mg/24 hours, 5 cm$^2$) to the healthy adults in the period 1 (3 days), followed by a washout-period for 7 days, and then administer the transdermal patch of the present invention (4.6 mg/24 hours, 5 cm$^2$) to the healthy adults in the period II (3 days). Another one of the sequences was to administer the transdermal patch of the present invention to the healthy adults in the period I (3 days), followed by a washout-period for 7 days, and then Exelon® was administered in the period II (3 days). Blood samples of each healthy adult were collected at different time points (1, 3, 6, 8, 10, 12, 14, 16, 18, 24, 26, 28, 32, and 36 hours) after administration, so that the drug concentrations in the blood were determined. Descriptive statistics of the obtained pharmacokinetic parameters were shown in Table 2.

TABLE 2

| Pharmacokinetic parameters | Transdermal patch of the present invention | | | Exelon ® | | |
|---|---|---|---|---|---|---|
| | Mean | SD | % CV | Mean | SD | % CV |
| $T_{max}$ (hr) | 16.6 | 5.53 | 33.2 | 15.7 | 5.04 | 32.1 |
| $C_{max}$ (ng/mL) | 2.43 | 0.968 | 39.8 | 2.57 | 1.29 | 50.2 |
| $AUC_{0-\infty}$ (hr*ng/mL) | 47.0 | 20.7 | 44.1 | 48.8 | 21.3 | 43.6 |
| $AUC_{0-t}$ (hr*ng/mL) | 47.3 | 20.7 | 43.7 | 49.2 | 21.3 | 43.3 |
| $AUC_{0-t}/AUC_{0-\infty}$ | 0.991 | 0.00413 | 0.417 | 0.991 | 0.00402 | 0.406 |
| $MRT_{inf}$ (hr) | 16.9 | 1.45 | 8.61 | 16.3 | 1.34 | 8.24 |
| $T_{1/2}$ (hr) | 2.57 | 0.284 | 11.0 | 2.63 | 0.229 | 8.69 |

% CV: % coefficient of variation

The transdermal patch of the present invention had similar bioavailability as compared to the control group of Exelon®.

TEST EXAMPLE 4

Skin Testing

To determine whether the transdermal patch of the present invention has similar properties of skin adhesion, skin irritation and skin sensitization to the commercial Exelon®, the properties of skin adhesion, skin irritation and skin sensitization for the transdermal patch of the present invention and Exelon® were observed when the bioequivalence trial of Test Example 3 was conducted.

Skin Adhesion Testing

In the skin adhesion testing, 28 healthy adults were tested and randomly divided into two sequences as described in the aforementioned Test Example 3. One of the sequences was to administer Exelon® (4.6 mg/24 hours, 5 cm$^2$) to the healthy adults in the period I (3 days), followed by a washout-period for 7 days, and then administer the transdermal patch of the present invention (4.6 mg/24 hours, 5 cm²) to the healthy adults in the period II (3 days). Another one of the sequences was to administer the transdermal patch of the present invention to the healthy adults in the period I (3 days), followed by a washout-period for 7 days, and then Exelon® was administered in the period II (3 days). The adhesion level of the patch for each healthy adult was observed at different time points (12 and 24 hours) after administration and scored according to the adhesion level. The results of the skin adhesion were shown in the following Table 3.

TABLE 3

| | | Exelon® | | Transdermal patch of the present invention | |
|---|---|---|---|---|---|
| | | n | | | |
| | | 28 | | 28 | |
| | | Time (hour) | | | |
| | | 12 | 24 | 12 | 24 |
| Skin adhesion score | 0 | 28 | 28 | 28 | 26 |
| | 1 | 0 | 0 | 0 | 2 |
| | 2 | 0 | 0 | 0 | 0 |
| | 3 | 0 | 0 | 0 | 0 |
| | 4 | 0 | 0 | 0 | 0 |

Adhesion score system:
0 = ≥90% adhered (essentially no lift off the skin)
1 = ≥75% to <90% adhered (some edges only lifting off the skin)
2 = ≥50% to <75% adhered (less than half of the patch lifting off the skin)
3 = >0% to <50% adhered but not detached (more than half of the patch lifting off the skin without falling off)
4 = 0% adhered - patch detached (patch completely off the skin)

As shown in Table 3, the transdermal patch of the present invention had excellent adhesion and its skin adhesion was similar to that of the commercial Exelon®.

Skin Irritation Testing

In the skin irritation testing, 28 healthy adults were tested and randomly divided into two sequences as described in the aforementioned Test Example 3. One of the sequences was to administer Exelon® (4.6 mg/24 hours, 5 cm²) to the healthy adults in the period I (3 days), followed by a washout-period for 7 days, and then administer the transdermal patch of the present invention (4.6 mg/24 hours, 5 cm²) to the healthy adults in the period II (3 days). Another one of the sequences was to administer the transdermal patch of the present invention to the healthy adults in the period I (3 days), followed by a washout-period for 7 days, and then Exelon® was administered in the period II (3 days). The irritation level of the patch for each healthy adult was observed at different time points (0, 24, 28, 32 and 36 hours) after administration and scored according to the irritation level. The results of skin irritation were shown in the following Table 4.

TABLE 4

| | | Exelon® | | | | | Transdermal patch of the present invention | | | | |
|---|---|---|---|---|---|---|---|---|---|---|---|
| | | n | | | | | | | | | |
| | | 28 | | | | | 28 | | | | |
| | | Time (hour) | | | | | | | | | |
| | | 0 | 24 | 28 | 32 | 36 | 0 | 24 | 28 | 32 | 36 |
| Skin irritation score | 0 | 28 | 14 | 4 | 14 | 21 | 28 | 16 | 9 | 16 | 23 |
| | 1 | 0 | 14 | 24 | 14 | 7 | 0 | 12 | 19 | 12 | 5 |
| | 2 | 0 | 0 | 0 | 0 | 0 | 0 | 0 | 0 | 0 | 0 |
| | 3 | 0 | 0 | 0 | 0 | 0 | 0 | 0 | 0 | 0 | 0 |

TABLE 4-continued

| | | Exelon® | | | | | Transdermal patch of the present invention | | | | |
|---|---|---|---|---|---|---|---|---|---|---|---|
| | | n | | | | | | | | | |
| | | 28 | | | | | 28 | | | | |
| | | Time (hour) | | | | | | | | | |
| | | 0 | 24 | 28 | 32 | 36 | 0 | 24 | 28 | 32 | 36 |
| | 4 | 0 | 0 | 0 | 0 | 0 | 0 | 0 | 0 | 0 | 0 |
| | 5 | 0 | 0 | 0 | 0 | 0 | 0 | 0 | 0 | 0 | 0 |

0 = No evidence of irritation
1 = Minimal erythema, barely perceptible
2 = Definite erythema, readily visible; or minimal edema; or minimal popular response
3 = Moderate, clearly defined erythema
4 = Severe erythema, with or without infiltration
5 = Severe erythema with vesicles or bullous reaction As shown in Table 4, the performance of the transdermal patch of the present invention was superior to Exelon® at time points of 24, 28, 32, and 36 hours after administration. For example, it could be observed that only 19 subjects administrated with the transdermal patch of the present invention had minimal erythema (barely perceptible), whereas 24 subjects administrated with Exelon® had minimal erythema (barely perceptible). Therefore, the patch of the present invention had low skin irritation.

Skin Sensitization Testing

In the skin sensitization testing, 28 healthy adults were tested and randomly divided into two sequences as described in the aforementioned Test Example 3. One of the sequences was to administer Exelon® (4.6 mg/24 hours, 5 cm²) to the healthy adults in the period I (3 days), followed by a washout-period for 7 days, and then administer the transdermal patch of the present invention (4.6 mg/24 hours, 5 cm²) to the healthy adults in the period II (3 days). Another one of the sequences was to administer the transdermal patch of the present invention to the healthy adults in the period I (3 days), followed by a washout-period for 7 days, and then Exelon® was administered in the period II (3 days). The sensitization level of the patch for each healthy adult was observed at 24 hours after administration and scored according to the sensitization level. The results of skin sensitization were shown in the following Table 5.

TABLE 5

| | | Exelon® | Transdermal patch of the present invention |
|---|---|---|---|
| | | n | |
| | | 28 | 28 |
| | | Time (hour) | |
| | | 24 | 24 |
| Skin sensitization score | 0 | 27 | 24 |
| | 1 | 1 | 4 |
| | 2 | 0 | 0 |
| | 3 | 0 | 0 |
| | 4 | 0 | 0 |

0 = No feeling about patch
1 = Slight irritation, do not eager to remove the patch from skin
2 = Slight irritation, eager to remove the patch from skin
3 = Moderate irritation, do not eager to remove the patch from skin
4 = Moderate irritation, eager to remove the patch from skin
5 = Severe irritation As shown in Table 5, the transdermal patch of the present invention had low sensitization and its skin sensitization was similar to that of the commercial Exelon®.

In summary, the transdermal patch of the present invention has good skin adhesion, low skin irritation, and low skin sensitization. In addition, the Exelon® consists of a backing layer, a drug-containing layer, an adhesive layer and a release liner, the drug-containing layer and the adhesive layer are separated, requiring two coating processes, so that its preparation process is complicated. The drug-containing adhesive layer of the transdermal patch according to the present invention comprises a drug and an adhesive, so that it is unnecessary to separately prepare the drug-containing layer and adhesive layer. Therefore, the manufacturing process is simple, saving time and cost, and is favorable for mass production. In addition, the transdermal patch of the present invention has a similar bioequivalence to that of Exelon®, and the present invention provides customers with another option.

Although the present invention has been explained in relation to its preferred embodiment, it is to be understood that many other possible modifications and variations can be made without departing from the spirit and scope of the invention as hereinafter claimed.

What is claimed is:

1. A transdermal patch, comprising:
    a backing layer;
    a drug-containing adhesive layer, comprising: rivastigmine or a pharmaceutically acceptable salt thereof, an adhesive, and two kinds of skin penetration enhancers; and
    a release liner,
    wherein the drug-containing adhesive layer is disposed between the backing layer and the release liner, a content of rivastigmine or the pharmaceutically acceptable salt thereof is in a range from 10 wt% to 30 wt% based on a total weight of the drug-containing adhesive layer, the adhesive comprises a pressure sensitive adhesive, and the two kinds of skin penetration enhancers are diethylene glycol monoethyl ether and glyceryl monooleate.

2. The transdermal patch according to claim 1, wherein a content of the adhesive is in a range from 50 wt% to 80 wt% based on the total weight of the drug-containing adhesive layer.

3. The transdermal patch according to claim 1, wherein the pressure sensitive adhesive is an acrylic-based pressure sensitive adhesive.

4. The transdermal patch according to claim 1, wherein a content of the two kinds of skin penetration enhancers is in a range from 0.1 wt% to 10 wt% based on the total weight of the drug-containing adhesive layer.

5. The transdermal patch according to claim 1, wherein the drug-containing adhesive layer further comprises a tacking agent.

6. The transdermal patch according to claim 5, wherein a content of the tacking agent is in a range from 0.1 wt% to 10 wt% based on the total weight of the drug-containing adhesive layer.

7. The transdermal patch according to claim 5, wherein the tacking agent is a resin.

8. A transdermal patch, comprising:
    a backing layer;
    a drug-containing adhesive layer, comprising:
        10-30 wt% of rivastigmine or a pharmaceutically acceptable salt thereof;
        50-80 wt% of an acrylic-based pressure sensitive adhesive;
        0.1-10 wt% of two skin penetration enhancers; and
        0.1-10 wt% of a tacking agent; and
    a release layer,
    wherein the drug-containing adhesive layer is disposed between the backing layer and the release liner, and the two kinds of skin penetration enhancers are diethylene glycol monoethyl ether and glyceryl monooleate.

9. The transdermal patch according to claim 8, wherein the tacking agent is a resin.

* * * * *